United States Patent
Simpson et al.

(10) Patent No.: US 9,486,138 B2
(45) Date of Patent: Nov. 8, 2016

(54) PORTABLE HANDHELD MEDICAL DIAGNOSTIC DEVICE HAVING A MEZZANINE CIRCUIT BOARD WITH A UNIVERSAL CONNECTION INTERFACE

(75) Inventors: Joseph M. Simpson, Fishers, IN (US); James D. Tenbarge, Fishers, IN (US); Ricky L. Collins, Cicero, IN (US); Blaine Edward Ramey, Indianapolis, IN (US); Matthew Carlyle Sauers, Indianapolis, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 1294 days.

(21) Appl. No.: 12/365,978

(22) Filed: Feb. 5, 2009

(65) Prior Publication Data

US 2010/0198032 A1    Aug. 5, 2010

(51) Int. Cl.
| | | |
|---|---|---|
| *A61B 5/00* | (2006.01) | |
| *A61B 5/145* | (2006.01) | |
| *H04B 7/00* | (2006.01) | |
| *G01N 33/487* | (2006.01) | |
| *A61B 5/01* | (2006.01) | |
| *A61B 5/024* | (2006.01) | |
| *A61B 5/11* | (2006.01) | |

(52) U.S. Cl.
CPC ....... *A61B 5/0002* (2013.01); *G01N 33/48785* (2013.01); *A61B 5/01* (2013.01); *A61B 5/024* (2013.01); *A61B 5/11* (2013.01); *A61B 5/145* (2013.01); *A61B 5/14532* (2013.01); *A61B 2560/04* (2013.01)

(58) Field of Classification Search
None
See application file for complete search history.

(56) References Cited

U.S. PATENT DOCUMENTS

| | | |
|---|---|---|
| 5,678,562 A | 10/1997 | Sellers |
| 5,876,351 A | 3/1999 | Rohde |
| 5,899,855 A | 5/1999 | Brown |
| 6,730,025 B1 | 5/2004 | Platt |
| 6,932,618 B1 | 8/2005 | Nelson |
| 6,936,008 B2 | 8/2005 | Tarakei et al. |
| 7,214,068 B2 | 5/2007 | Kronich et al. |
| 2007/0258395 A1* | 11/2007 | Jollota et al. ............... 370/310 |
| 2010/0052915 A1* | 3/2010 | Allen et al. ............... 340/573.1 |
| 2010/0186081 A1* | 7/2010 | Kawate ........................ 726/17 |
| 2010/0228111 A1* | 9/2010 | Friman et al. ............... 600/365 |

OTHER PUBLICATIONS

Haller, The ZEN of BDM, Macraigor Systems, Inc., 1996-1997, pp. 1-15, Brookline Village, MA, USA.
ANT11TR41x Transceiver Chipset, Dynastream Innovations Inc., 2007, Revision 1.2, pp. 1-19, Cochrane, Alberta, Canada.
Draft Standard for a Common Mezzanine Card Family: CMC, IEEE Standards Department, P1386/Draft 2.4a, Mar. 21, 2001, pp. i-49, Piscataway, NJ, USA.
MC9S08JM60, MC9S08JM32 Data Sheet, HCS08 Microcontrollers, Rev. 2 Mar. 2008, www.freescale.com, pp. 1-386.
SlimStack SMT Board-to-Board Connector Family, Molex catalog, www.molex.com, pp. 1-8, Molex Japan 2006.
FreeStyle Navigator Continuous Glucose Monitoring System, Abbott Diabetes Care, pp. 1-2, 2008.
Accu-Chek Aviva Blood Glucose Meter Owner's Booklet, Roche Diagnostics Operations, Inc., pp. 1-92.
FreeStyle Navigator Continuous Glucose Monitoring System, Abbott Diabetes Care, pp. 1-196, 2008.
MXP430xG461x Mixed Signal Microcontroller, Apr. 2006, Revised Oct. 2007, pp. 1-106, Texas Instruments, Dallas, TX, USA.

* cited by examiner

*Primary Examiner* — David Thomas
(74) *Attorney, Agent, or Firm* — Harness, Dickey

(57) ABSTRACT

A portable handheld medical diagnostic device capable of communicating with an external device and a method thereof are disclosed. The device has a protective enclosure, a main circuit board provided in the protective enclosure and having a wireless connectivity component and a controller facilitating a physiologic measurement and communications of results of the physiological measurement to the external device. Also provided in the protective enclosure is a mezzanine circuit board having at least one of a plurality of additional feature modules and a universal connection interface programmed to both facilitate operation of the additional feature module and operate under the control of the controller as a control interface between the controller and the additional feature module.

40 Claims, 5 Drawing Sheets

US 9,486,138 B2

PORTABLE HANDHELD MEDICAL DIAGNOSTIC DEVICE HAVING A MEZZANINE CIRCUIT BOARD WITH A UNIVERSAL CONNECTION INTERFACE

FIELD OF THE INVENTION

The present invention relates generally to portable, handheld medical devices, and in particular a portable, handheld medical diagnostic device having a mezzanine circuit board with a universal connection interface.

BACKGROUND OF THE INVENTION

Device communication (wired and wireless), especially between portable, handheld medical diagnostic devices and a host system of a health care provider, is an important part of a health care regime. Providing wireless connectivity between the portable handheld medical diagnostic device, such as a personal blood glucose meter, and a host system can take many forms. For example, the following types of wireless connectivity, which have been employed by such portable handheld diagnostic medical diagnostic devices, include Bluetooth (Ultra low power), ZigBee, Certified Wireless USB, Near Field Communication (NFC), Active RFID, Wi-Fi, and IrDA. Typically, due to legal, engineering and cost factors, such medical diagnostic devices are only manufactured with a single type of wireless connectivity.

However, as the methods of wireless communications continue to evolve, the solution to providing medical diagnostic devices with additional features and/or a new type of wireless connectivity often takes two forms, either an add-on solution or an integrated solution. For the integrated solution, the integration of a new connectivity means into an existing portable handheld medical diagnostic device requires redesign and redevelopment of a new model of the medical diagnostic device. Such redesigns and redevelopments require significant costs and a long development and approval process.

For the add-on solution, an adapter module is developed containing the additional feature or the new wireless connectivity means which normally attaches to an external surface of the existing medical diagnostic device. The advantage of this solution is that the add-on module provides minimal impact to the operation and configuration of the medical diagnostic device. However, typical add-on solutions require user interaction to initiate either the additional feature or the wireless connectivity by pressing buttons on both devices, as is the case for conventional blood glucose meters. In addition, in the case of portable handheld blood glucose meters, there is currently no automatic method for muting a transmitter during a patient measurement, which can cause measurement errors in some such meters. Furthermore, some such add-on adaptors cannot be electrically isolated during recharging thereby increasing the risk to device damage from a short. Finally, different versions of such add-on adapters are often needed in order to adapt with different medical diagnostic device configurations thereby adding to production costs.

SUMMARY OF THE INVENTION

It is against the above background that in one embodiment a portable handheld medical diagnostic device having a mezzanine circuit board with a universal connection interface that reduces product development time and compartmentalizes costs to each optionally added feature is disclosed. In one embodiment a flexible/open integrated solution that enables users the ability to easily choose and add a connectivity option and additional features to a base design of the portable handheld medical diagnostic device through a provided universal connection interface is disclosed. Various embodiments of the invention permit manufacturers to add connectivity options to the base design during the manufacturing process in order to provide a line of medical diagnostic devices each having their own "favor of feature(s)" from the one base design. The present invention allows for faster time to market with the common base design, namely a main circuit board, of the portable handheld medical diagnostic device having already been developed and approved, therefore subsequent feature additions to the device, via a mezzanine board interconnected with the main board, will have reduced development and approval cycle time.

In one embodiment, a portable handheld medical diagnostic device capable of communicating with an external device is disclosed. The device comprises a protective enclosure, and a main circuit board provided in the protective enclosure and having a wireless connectivity component and a controller facilitating a physiologic measurement and communications of results of the physiological measurement to the external device. A mezzanine circuit board is provided in the protective enclosure and has at least one of a plurality of additional feature modules, and a communications microcontroller programmed to facilitate operation of the at least one additional feature module and to operate under the control of the controller as a control interface between the controller and the at least one additional feature module.

In another embodiment, a method of establishing communications with external wireless device via a portable handheld medical diagnostic device having a main circuit board provided with a controller facilitating a physiologic measurement and communications of results of the physiological measurement to the external wireless device, a mezzanine circuit board having a wireless connection controller, and a communications microcontroller programmed to both facilitate operation of the wireless connection controller and to operate under the control of the controller as a control interface between the controller and the wireless connection controller is disclosed. The method comprises having the microcontroller perform a status check with the communications microcontroller to see if a communication connection between the external wireless device and the wireless connection controller is provided. If the status check is no, then the method comprises having the microcontroller automatically place the wireless connection controller in a discovery mode wherein the wireless connection controller responses to connection inquires from the external wireless device with a device name in order to identify the diagnostic device to the external wireless device, and wherein the discovery mode is enabled by the controller sending the communications microcontroller a control command to enter the discovery mode to which the microcontroller acknowledges and turns on the wireless connection controller.

In still yet another embodiment, a portable handheld medical diagnostic device capable of communicating with an external device is disclosed. The device comprises a protective enclosure, and a main circuit board provided in the protective enclosure and having a wireless connectivity component and a controller facilitating a physiologic measurement and communications of results of the physiological measurement to the external device. A mezzanine circuit board is provided in the protective enclosure and has at least one additional feature and communication means programmed to facilitate operation of the at least one additional feature and to operate under the control of the controller via control signal means.

These and other advantages and features of the invention disclosed herein, will be made more apparent from the description, drawings and claims that follow.

BRIEF DESCRIPTION OF THE DRAWINGS

The following detailed description of the embodiments of the present invention can be best understood when read in conjunction with the following drawings, where like structure is indicated with like reference numerals, and in which.

DETAILED DESCRIPTION

The following description of the preferred embodiment is merely exemplary in nature and is in no way intended to limit the invention or its application or uses.

Hardware Description

Figure 1B:
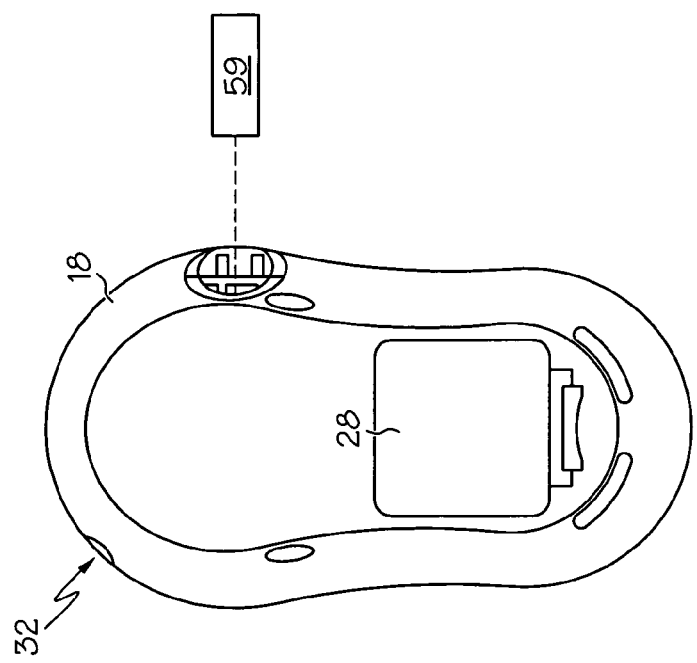
FIGS. 1A and 1B are front and back views, respectively, of a portable, handheld medical diagnostic device according to an embodiment of the present invention.
Figure 1A:
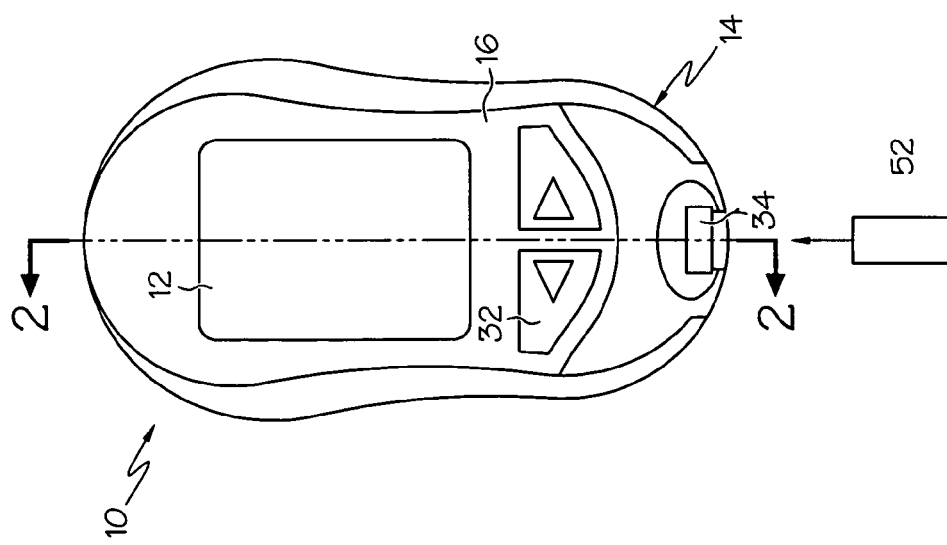

With reference to FIGS. 1A and 1B, the present invention in one embodiment is embodied in a portable, handheld medical diagnostic device 10 with a display 12 and having a protective enclosure, generally indicated by symbol 14, protecting electronics therein. The display 12 may be any conventional display device used in a portable, handheld electronic device, such as, for example, but not limited to LCD displays, LED displays, OLED displays, and other types of displays which may be heretofore developed. Further, display 12 may be any other variety of indicators, including, but not limited to a series of lights and/or other types of simple light devices as opposed to a single integrated display screen. The display 12 is used for electronically displaying graphics, text, and other elements to a user. In one embodiment, the display 12 is also a touch-screen user interface that is used with the tip of a finger of the user and/or a stylus or other touching device to select elements from the screen, to draw figures, and to enter text with a character recognition program running on the device 10. In still other embodiments, the device 10 may also include other types of output devices such as for example, sound devices, vibration devices, etc.

Figure 2:
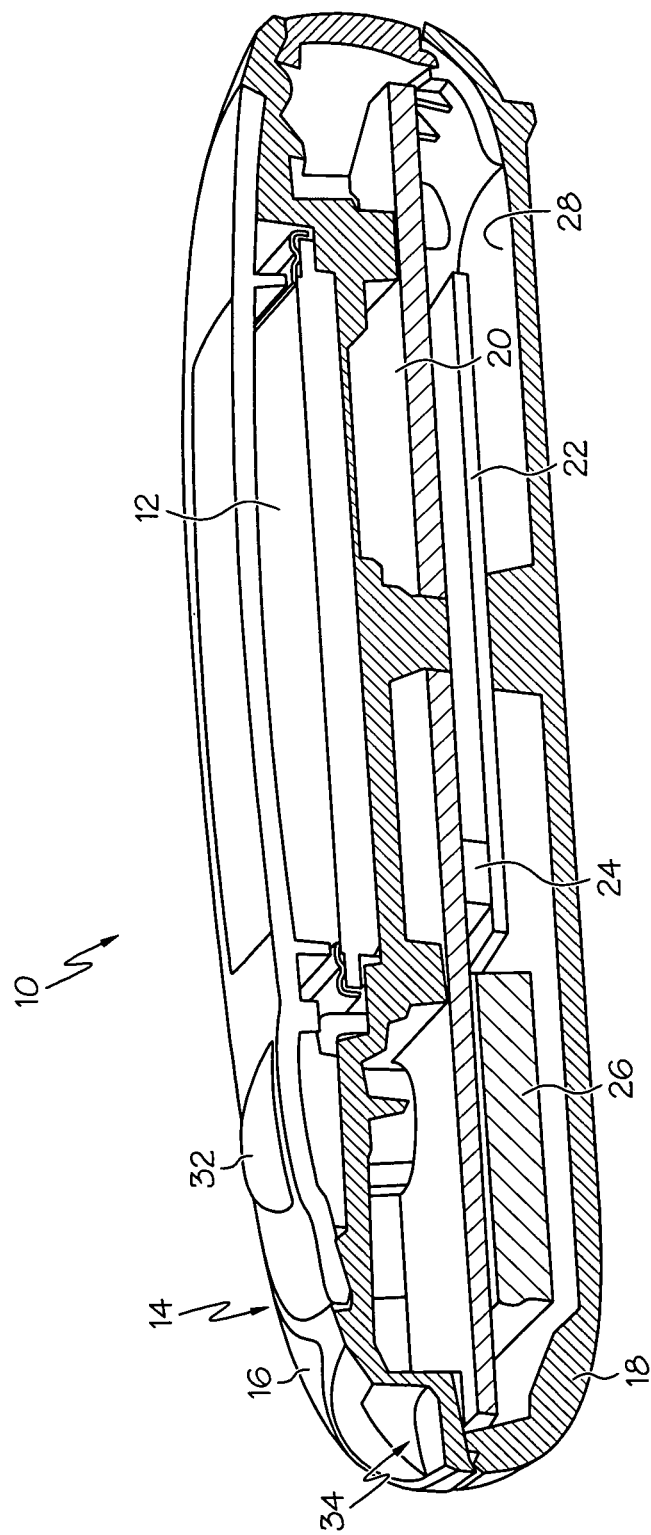
FIG. 2 is a side section view of the device of FIG. 1A taken along section line 2-2.

Reference hereafter is made also to FIG. 2, in which the protective enclosure 14 comprises a front housing 16 and rear housing 18. As shown, the housings 16 and 18 mate to form a protective shell for the internal components contained therein, such as for example, the display 12, main circuit board 20, and a mezzanine module circuit board 22.

Housings 16 and 18 may be formed from any of a variety of materials, including but not limited to polymeric materials, metals and metal alloys, etc. The internal components of the device 10 may be mounted in the protective enclosure 14 using many different mounting techniques. For example, in one embodiment, mounted via open or closed cell foam inserts provided in the protective enclosure 14, or in another embodiment, mounted via attaching the main circuit board 20 to an interior side of one of the housings 16 and 18 with a fastener. In another embodiment, the main circuit board may be mounted by a snap fit with an interior side of one of the housings 16 and 18.

As shown by FIG. 1, the main circuit board 20 and the mezzanine circuit board 22 electrically interface together via a board-to-board connector 24. The board-to-board connector in one embodiment provides a less than 0.8-inch space between major surfaces of the main circuit board 20 and the mezzanine circuit board 22. In one embodiment, the board-to-board connector 24 electrically connects the mezzanine circuit board 22 to the main circuit board 24 in a stacked fashion, which situates the major surfaces of both the main circuit board 20 and the mezzanine circuit board 22 in parallel planes and in close proximity within the protective enclosure 14. In one specific embodiment, the board-to-board connector is a surface mounted (SMT) board-to-board connector.

As best shown by FIG. 2, a power supply 26 is also provided within the protective enclosure 14 to provide power to the electrical/electronic components of the device 10. In one embodiment, the rear housing 18 provides a cavity 28, which is shaped to accommodate therein the mezzanine circuit board 22, the main circuit board 24, and the power supply 26. In other embodiments, the shape and dimensions of front and rear housings 16 and 18 of the protective enclosure 14 may vary for each manufacturer and model of the device 10.

In one embodiment, the mezzanine circuit board 22 provides components for a low power embodiment. In such an embodiment, the power supply 26 is a battery, and in particular, a coin cell, where in any RF based component that can be operated from the coin cell is considered low power (e.g., a FitLinxx or any other ULP wireless personal area network enabled device). In another embodiment, the mezzanine module circuit board 22 provides for a high power embodiment, wherein any RF component that cannot be operated from a coin cell is considered high power (e.g., a Bluetooth enabled device). In such a high power embodiment, the power supply 26 in one embodiment is a rechargeable battery such as, for example, a Li ion or Li polymer battery. Accordingly, the device 10 may include a rechargeable or non-rechargeable battery as the power supply 26.

In one embodiment, the power supply 26 is accessed and replaceable from the cavity 28 via a panel 30 provided in the rear housing 18 as best shown by FIG. 1B. In a rechargeable battery embodiment, the device 10 may be sealed permanently with the original batteries installed by the manufacturer. Additional power, such as for recharging the power supply 26, may be provided from a remote source of electricity that is transmitted to the device 10 through a wire cable or through other methods of electrical transmission. For example, and in one embodiment, the device 10 is rechargeable via a connected (wired) external device 27. It is to be appreciated that the device 10 provides a universal connection interface, discussed in a later section, which in one embodiment operates is a universal serial bus (USB) interface, and in another embodiment is a Firewire interface, and either of which provides a wired connector (i.e., connector 68) which connects to a charger (i.e., charger 78, FIG. 3) for charging the device 10 via the connected external device 27.

In one embodiment, the mezzanine circuit board 22 provides system voltage regulation. In the embodiment where the power supply is a coin cell battery, a regulator 80 (FIG. 3) may be provided for devices on the mezzanine circuit board 22 that have a limited supply voltage range. In one embodiment, the power supply is a 5V power supply capable of providing initially 100 mA. In the embodiment where the power supply 26 is a rechargeable battery the regulator 80 is provided.

In still other embodiments, the electronic device 10 may have indicator lights, such as status lights for power, communication, battery status, or other functions. The lights may be located on any of the sides of the device, and may be viewable on one or more sides.

A user interface 32 is also provided to operate and interact with the features of the device 10. In one embodiment, the user interface 32 of the device 10 may include at least one button or combination of buttons (e.g., on/off button, left and right buttons), such as for power, program navigation, selection, and data entry. As shown, the user interface 32 in one embodiment is provided on the front housing 16 of the device 10 adjacent the display 12. In one embodiment, the device 10 provides an OK button, a right button, a left button, and/or joy stick/track ball, which a user uses to navigate through a software drive menu provided on the display 12. In other embodiments, additional buttons may be used as shortcut buttons to call up a certain program on the device 10, may comprise a method of scrolling, may be used to select items from a list, or may have any function that the software designer of the device may assign to the button or set of buttons. Each button size, layout, location, and function may vary for each manufacturer and model of the device 10.

In one embodiment, the main circuit board 20 is designed so only core components that provide for the operation of the device 10 as a medical diagnostic device is provided thereon. The additional components necessary for adding optional features beyond the core components are provided by the mezzanine circuit board 22. Such optional features, which may be provided by the mezzanine circuit board 22, include components or modules providing additional wireless connectivity, speech emulation/recognition, a voice recorder, RF telemetry, GPS, additional memory, a camera, battery-charging/additional power, and combinations thereof. The additional wireless connectivity component, module, or chip may be a Bluetooth system, a ZigBee system, a Certified Wireless USB system, a Near Field Communication (NFC) system, an Active RFID system, a Wi-Fi system, an IrDA device, and combinations thereof. A common firmware base for the main circuit board 20 can thus be provided which can then be used as well across all the different types of mezzanine circuit boards 22 each providing various additional features. It is to be appreciated that the mezzanine circuit board 22 can provide any variety of wireless connectivity and retain the identical electrical connection and mechanical footprint to allow any such module to fit and work with the cavity 28 of the device 10.

In one embodiment, the device 10 is an in vitro diagnostic device that is used to test blood and other body fluids and tissues to obtain information for the diagnosis, prevention and treatment of a disease. In another embodiment, the device 10 is a self-testing blood glucose meter for people with diabetes and in another embodiment, the device 10 may be a point-of-care (POC) testing device. In one embodiment, the device 10 is a handheld reagent-based blood glucose meter, which measures glucose concentration by observing some aspect of a chemical reaction between a reagent and the glucose in a fluid sample. The reagent is a chemical compound that is known to react with glucose in a predictable manner, enabling the monitor to determine the concentration of glucose in the sample. For example, the meter may be configured to measure a voltage or a current generated by the reaction between the glucose and the reagent.

A small test strip is often employed to hold the reagent and to host the reaction between the glucose and the reagent mentioned above. Accordingly, in one embodiment of the device 10 as a blood glucose meter, the protective enclosure 14 is provided with a strip port 34 for inserting a test strip into the electronic device 10. The strip port 34 is used such that the reaction between the glucose and the reagent may be read electronically in order for the device 10 to determine the concentration of glucose in the sample. These embodiments enable both health care professionals and patients to perform reliable decentralized testing in hospitals, clinics, offices or patients' homes. In other embodiments, the device 10 may form part of or include coagulation monitoring systems, professional blood glucose testing and monitoring systems, cardiac marker testing devices, blood gas/electrolyte testing, and urinalysis screening products.

Figure 3:
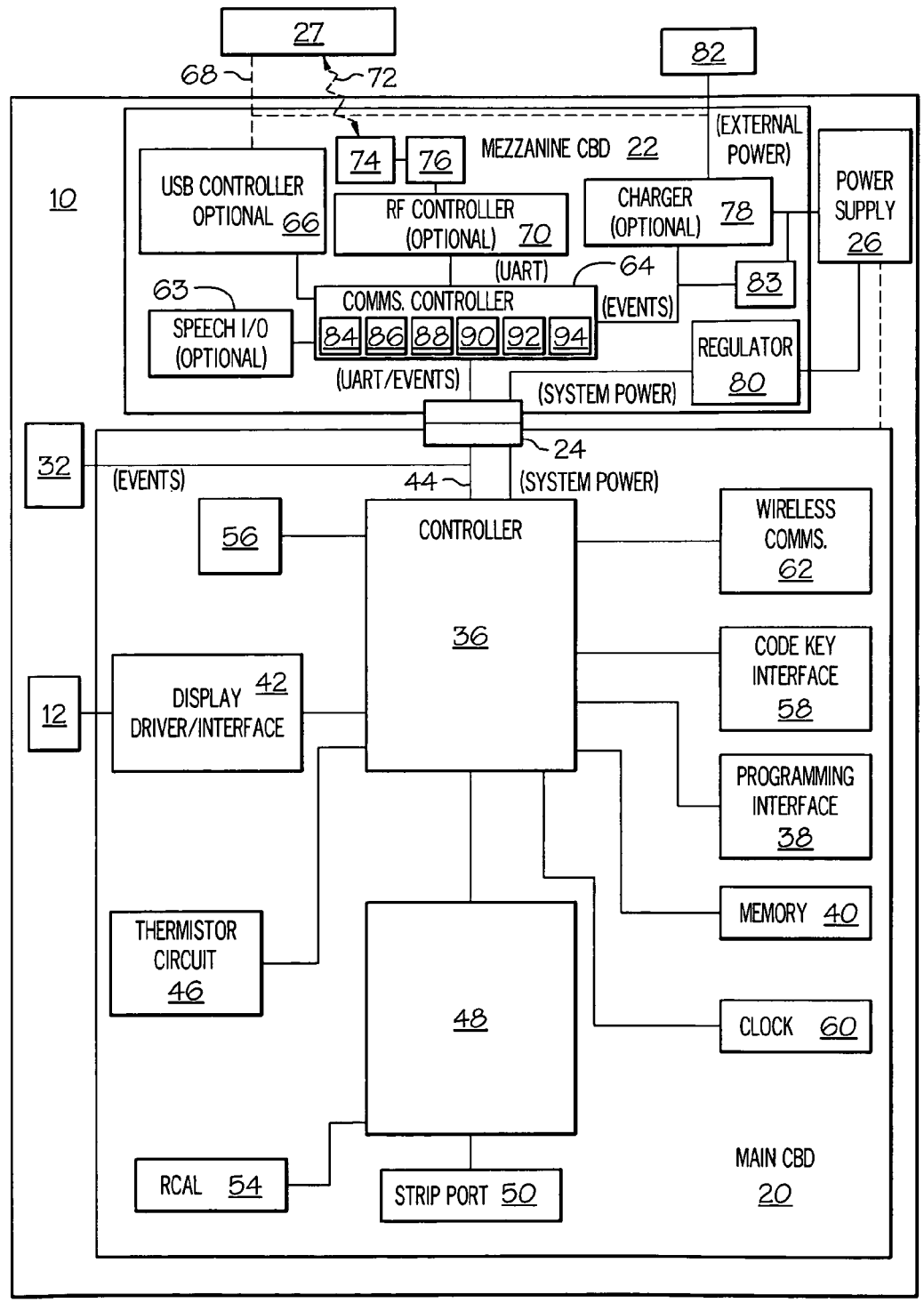
FIG. 3 is a system block diagram of a portable, handheld medical diagnostic device according to an embodiment of the present invention.

With reference to FIG. 3, a block diagram showing the hardware components and interfaces according to various embodiments of the present invention is provided. In one embodiment and as previously mentioned above, the main circuit board 20 is designed so only core components that provide for the operation of the device 10 as a medical diagnostic device is provided thereon. For example, in one embodiment the main circuit board 20 includes a measurement engine and user interface controller, hereinafter referred to as controller 36. In one embodiment, the controller 36 is a programmable mixed signal microcontroller (e.g. Texas Instruments MSP 430). The controller 36 provides integrally an n-bit RISC CPU (where n is greater than or equal to 16), an n-bit registers (where n is greater than or equal to 16), and a digitally controlled oscillator (DCO) which allows for wake-up from a low-power mode to an active mode in less than 6 µs. The controller 36 also provides in one embodiment at least two bit timers, at least one high-performance n-bit A/D converter (where n is greater than or equal to 12), at least two dual n-bit D/A converters (where n is greater than or equal to 12), at least three configurable operational amplifiers, at least one universal serial communication interface (USCI), at least one universal synchronous/asynchronous communication interface (USART), DMA, input/output (I/O) pins, and a liquid crystal display (LCD) driver with a regulated charge pump. In other embodiment, other mixed signal microcontroller and/or microprocessors may similarly be used, including those made or provided by different manufacturers.

The main circuit board 20 also includes a programming interface 38 to configure and control the controller 36 via software, e.g., firmware providing boot-up, device drivers, and application instructions. The programming interface 38 in one embodiment provides for boot loading of software code to internal memory, such as for example, flash memory (e.g., EEPROM) 40, and in another embodiment further provides a testing pad (e.g., JTAG) to permit in-circuit testing and debugging of hardware devices, such as according to IEEE standard number 1149, "Standard Test Access Port and Boundary-Scan Architecture." In still other embodiments, the firmware may be embedded in other memory provided by the device 10, the controller, and/or any other components of the main circuit board 20 having internal memory. In other embodiments and in addition, the flash memory 40 can be programmed via the testing pad, a bootstrap loader via the USART (serial) interface, or in system by the controller 36.

As shown by FIG. 3, the main circuit board 20 in one embodiment also provides a display connector interface 42 (e.g., LCD pads) which is controlled by the controller 36 via instructions from the display driver and application software, such as loaded from memory 40. In still another embodiment, the main circuit board 20 provides input to the controller 36 via a peripheral interface 44 which interconnects such as, for example, with the user interface 32 and/or wired communications such as, for example, keyboard input, serial port and parallel port input and output, such as to another computer, test equipment, printers, and the likes. A thermistor circuit (temperature sensor) 46 is also provided in one embodiment which is used to measure the local temperature which is important in determining glucose level of a patient when the device is provided as a glucose meter.

In the glucose meter embodiment, the main circuit board 20 provides a strip reader 48 connected to a strip connector interface or strip port 50. In one embodiment, the strip reader 48 is a second programmable mixed signal microcontroller (e.g. Texas Instruments MSP 430) specifically configured (e.g., application specific integrated circuit (ASIC)) to sample and read a disposable test strip 52 provided to the strip port 50. The strip port 50 is used to connect the test strip 52 electrically to the strip reader 48, which reads the test strip electronically in one of the manners mentioned above previously and provides such input to the controller 36 for analysis.

A calibration resistor 54 may be provided on the main circuit board and used to provide a calibration value to the strip reader 48 as well as a sound device 56 to indicate readiness for test strip reading and/or successful/unsuccessful reading of the test strip 52. In one embodiment, the controller 36 using the inputs from the thermistor circuit 46 and the test strip 52, via the strip port 50 and strip reader 48, then calculates the glucose level and the results of a patient's glucose measurement displayed on the display 12. It is to be appreciated that since the flash memory 40 is in-system programmable, a portion of the flash memory 40 in one embodiment is used to data-log the patient's glucose measurements.

A code key interface 58 may also be provided which is used to provide calibration data to the controller 36 via a code key chip 59 (FIG. 1B) and which is used in the measurement of the test strip 52 (FIG. 1A) and in the calculation used to compute the glucose level. A clocking element 60, such as for example, a 32 kHz crystal, is also provided on the main circuit board 20 for sampling timing performed by the strip reader 48 and by an integrated digitally controlled oscillator to generate a high-speed clock required for the controller 36 and the other provided peripherals requiring a clock.

Finally, the main circuit board 20 in one embodiment provides a wireless connectivity component 62 which is used for calibration, configuration, and/or communicate with other devices such as, for example, another meter, an insulin pump, a printer, a router/modem, and/or a PC. In one embodiment, the wireless connectivity component 62 provides infrared communications. In such an embodiment, the device 10 communicates with a PC running a compatible software package such as, for example, Roche Diagnostic's Accu-Chek Compass diabetes care software via an IrDA-serial port adapter. Such an embodiment permits a user to download data from the device 10 via the IR based wireless connectivity component 62 and stores results to the PC. In other embodiments, the wireless connectivity component (or module) 62 may be a Bluetooth system, a ZigBee system, a Certified Wireless USB system, a Near Field Communication (NFC) system, an Active RFID system, a Wi-Fi system, and combinations thereof.

As mentioned previously above, the main circuit board 20 interfaces with the mezzanine circuit board 22 via the universal connecter 24. As shown by FIG. 3, the mezzanine circuit board 22 provides the universal connection interface implemented as a communications microcontroller 64. In one embodiment the communications microcontroller 64 is a low-cost, high-performance HCS08 Family of n-bit microcontroller units (where n is greater than or equal to 8) that is provided with a variety of modules, memory sizes, memory types, and package types. In one particular embodiment, the communications microcontroller 64 is a Freescale Semiconductor MC9S08JM60 chip providing an enhanced HCS08 central processing unit core programmable via HC08 instructions, and providing an internal addressable bus with on-chip in-circuit programmable flash memory. In other embodiments, other microcontrollers and/or microprocessors may similarly be used, including those made or provided by different manufacturers, such as for example, a Motorola low-power HCS08 based microcontroller as the universal connection interface. It is to be appreciated that the communications microcontroller 64 implements the universal connection interface by being able to operate and communicate with a variety of additional feature components that may be implemented on the mezzanine circuit board 22 according to a desired manufacturing design flavor or type. In particular, as the communications microcontroller 22 functions as the universal connection interface (i.e., go between) for the controller 36 on the main circuit board 20 and the implemented additional feature component(s) e.g., a wired connection controller, a wireless connection controller, a charger 78, a voice recognition module 63, and combinations thereof provided on the mezzanine circuit board 22, no changes in the firmware of the device 10 is needed to implement these various flavors or types of the mezzanine circuit board 22, which are discussed hereafter.

In one embodiment, the communications microcontroller 64 operates and communicates with a wired connection controller 66 provided on the mezzanine circuit board 22. In one embodiment, the wired connection controller 66 is a Universal Serial Bus (USB) device controller with a dedicated on-chip USB transceiver. The USB device controller is based on the Universal Serial Bus Specification Rev 2.0, and in other embodiments may be based on any other or future specification revisions. In one particular embodiment, the wired connection controller 66 is an integrated USB module (S08USBV1) provided by the MC9S08JM60 chip. In other embodiments, the USB device controller 66 may be a discrete on board chip that is provided by the same or another manufacturer. In another embodiment, the wired connection controller 66 is a Firewire controller based on the IEEE Standard 1394. For these embodiments, the device 10 provides a cabinet hole in the housing 16, 18 such that a wired connector 68 from the external device 27 can connect to the wired connection controller 66.

In still another embodiment, the communications microcontroller 64 communicates and operates a wireless (e.g., radio frequency (RF)) connection controller 70 provided on the mezzanine circuit board. In one embodiment, the wireless connection controller 70 comprises a transceiver 74 that is controlled via an analog-to-digital converter (ADC)

microcontroller (MCU) 76 that passes data to and from the communications microcontroller 64. In one embodiment, the transceiver 74 is a low power transceiver such as, for example, a Nordic Semiconductor nRF24L01 or nRF24L01+ single chip 2.4 GHz transceiver having a range of about 30 to about 100 feet (10 to 30 m) and a data rate up to about 2 Mbit/s. In other embodiments, the transceiver 74 may a chip-based transceiver of other power requirements, frequencies, ranges and data rates that is provided by the same or another manufacturer. In one embodiment, the ADC MCU 76 is an n-bit ADC MCU, where n is greater than nine. In one particular embodiment, the ADC MCU 76 is a Silicon Laboratories C8051F931 chip, and in other embodiments is any other similar ADC MCU chip provided by another manufacture.

In other embodiments, the wireless connection controller 70 may be a Bluetooth system, a ZigBee system, a Certified Wireless USB system, a Near Field Communication (NFC) system, an Active RFID system, a Wi-Fi system, a FitLinxx system, and combinations thereof. In still another embodiment, the communications microcontroller 64 and wireless connection controller 70 may be a single chip providing the transceiver 74 and the ADC MCU 76 such as, for example, a Nordic Semiconductor nRF24Ex System on Chip (SoC) with an Intel based 8051 MCU.

In still another embodiment of the mezzanine circuit board 22, the communications microcontroller 64 controls a provided charger 78. The charger 78 is used in this embodiment to charge the power supply 26 which provides power also to the components of the mezzanine circuit board 22 and is controlled via the communications microcontroller 64. In one embodiment, the charger 78 is a power MOSFET chip with integrated sensing and control providing sufficient voltage to charge a lithium based battery, and in one particular embodiment is a Freescale Semiconductors MC34671 integrated battery charger chip. In other embodiments, the charger 78 may be a similar chip provided from any other manufacture. In one embodiment, the power supply 26 is a Li-Ion battery or a Li-Polymer battery(s) of either a single or multiple cells. The charger 78 provides input over-voltage-protection to the power supply 26 when being charged via an external power supply 82, and charge current and thermal monitoring.

The mezzanine circuit board 22 may also be provided in one embodiment with a battery gas gage 83 to indicate remaining available battery life of the power supply 26. In one embodiment, the battery gas gage is a TI BQ27200 chip and in other embodiments may be a similar chip provided by another manufacturer.

In still other embodiments, the mezzanine circuit board 22 may provide any combination of the above described additional feature components, i.e., the wired connection controller 66, the wireless connection controller 70, the charger 78, the battery gas gage 83, and other such additional feature components that are universally interfaced to the main circuit board 20 via the communications controller 64. In still other embodiments, the power supply 26 may be two power supplies each for powering a respective circuit board 20, 22. To describe further the features of the present invention, an illustrative embodiment having a specific configuration and modes of operation is now disclosed hereafter.

In one embodiment, the device 10 is configured as blood glucose meter in which the controller 36 of the main circuit board 20 functions to provide a blood glucose measurement and interfaces with the communications microcontroller 63 on the mezzanine circuit board 22. In one embodiment, the controller 36 and communications microcontroller 64 communicate serially through the board-to-board connector 24. In such an embodiment, the controller 36 is programmed to permit a user (patient) to initiate and perform a blood glucose (bG) test. In one embodiment, the controller 36 is programmed to indicate the status of the bG test as it proceeds via display interface 42 and as feedback to the communication microcontroller 64. Once the bG test has been successfully completed, the controller 36 will provide the bG test result to the user on the display 12 and to the communication microcontroller 64. In one embodiment, if so enabled by the user, the communication microcontroller 64 then transmit the results of the bG test to another device via the wired or wireless connection interface implemented and controlled through the wired or wireless connection controller 66 or 70, respectively. In one embodiment, the wired connection controller 66 supports data rates of up to 400 Mbps and the wireless connection controller 70 supports data rates of up to 2 Mbps. A discussion on the firmware interaction between the controller 36 and the communications microcontroller 64 is provided hereafter, such as, for example to implement the above-mentioned arrangement.

Firmware Interaction

It is to be appreciated that the microcontroller 64 of the mezzanine circuit board 22 acts as the communication controller to the "outside world" for the device 10 and allows a wide range of interface flexibility. In the embodiments that follow, three separate configuration modes of firmware (F/W) interaction of the main circuit board 20 to the mezzanine circuit board 22 is provided for discussion purposes. The first mode is referred to as a LOW F/W interaction configuration mode. In one embodiment, this mode may be used to set-up and communication data automatically to the external device with minimum instructions and operations between the controllers 36 and 64 of the device 10. In one embodiment, particular button presses of the user interface 32, such as for example, a double button press, results in the controller 36 instructing the communications microcontroller 64 to place the device 10 into a communications mode. For example, in one embodiment, when the device 10 is instructed by the user to enter the communications mode, the communications microcontroller 64 pairs with and instructs the wireless connection controller 70 to establish a wireless link in order to send and receive data. In another embodiment, the device 10 automatically detects a wired connection made thereto, such as, by a USB or Firewire device, and enters the communication mode therewith. In one embodiment, the device 10 when in the LOW F/W interaction configuration mode accepts commands from an external device, via the wired or wireless connection, running a compatible software application enabling and providing such commands.

The second configuration mode is a MEDIUM F/W interaction configuration mode. This configuration mode is a hybrid method and is intended to have the controller 36 squawk results data or error codes to the communications microcontroller 64 without user interaction. In this mode, after receiving data or an error code from the controller 36, the microcontroller 64 establishes the communications link and sends data to a receiving external device. This configuration mode also allows the user to enter into a pass through mode e.g., via a double button press or an insertion of a wired connection 68 in order to establish the communications link and take commands from the external device which is running a compatible software application enabling and providing such commands.

The third configuration mode is a HIGH F/W interaction configuration mode. This mode includes all of the features of the LOW and MEDIUM F/W interaction configuration modes, but permits the user to configure the level of interaction between the controller 36 and microcontroller 64 and the connected external device 27 (automatic, user initiated, etc.). In particular, this mode enables the highest level of integration (instructions/operations) between the controller 36 and microcontroller 64.

The above configuration modes are enabled by the addition of additional events and control signals to a conventional serial communications command set for hardware interfacing according to the embodiments of the present invention. The events and control signals also allow greater flexibility to implement future connectivity use case scenarios. The events and controls signals provided between the controller 36, the microcontroller 64, and the other additional feature components disclosed by FIG. 3 during each of the above-mentioned configuration modes are discussed hereafter with reference made also to FIG. 4.

Figure 4:
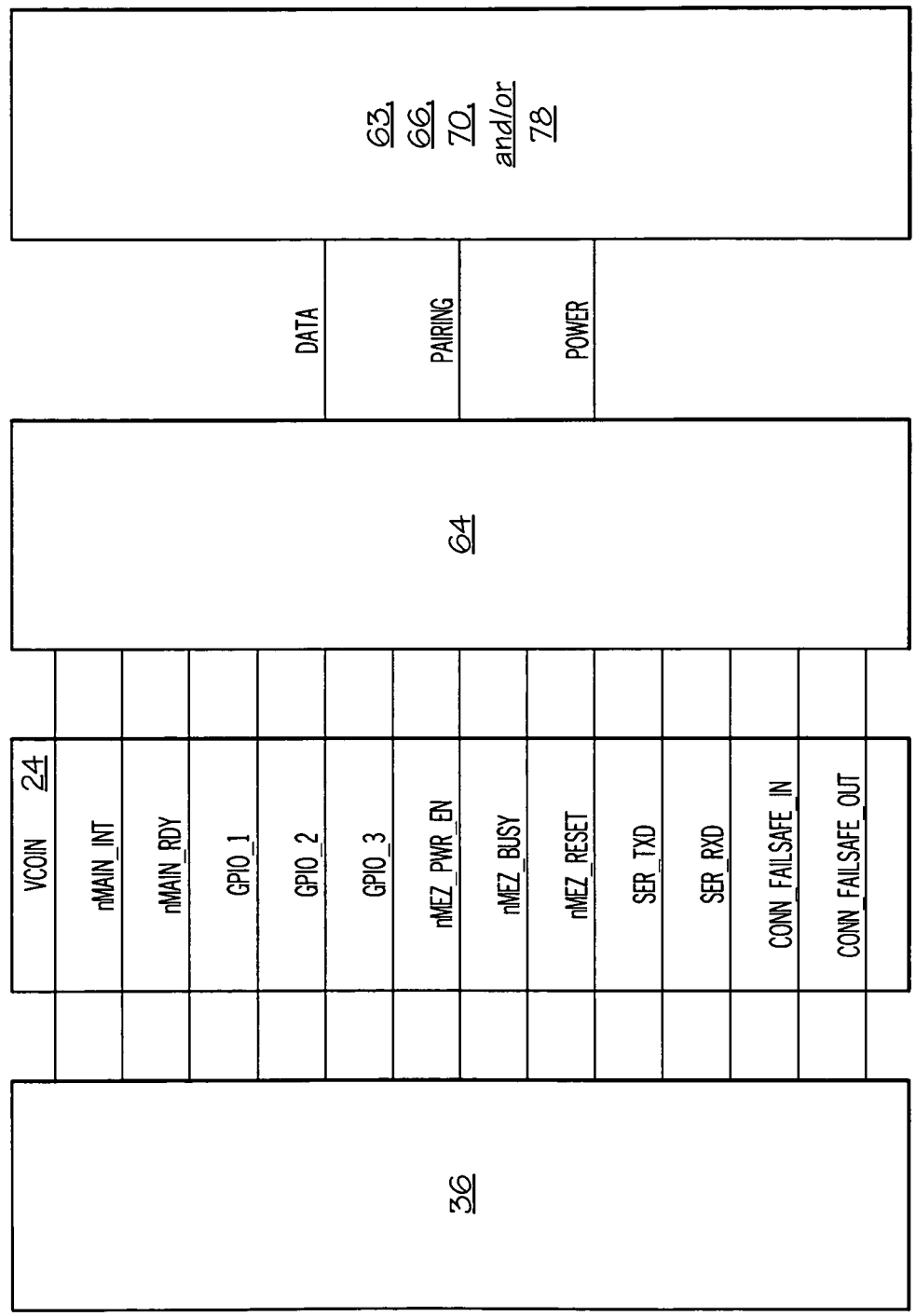
FIG. 4 is a system block diagram of a portable, handheld medical diagnostic device according to an embodiment of the present invention showing the various discrete signals provided between a main circuit board controller and a universal connection interface of a mezzanine circuit board through a board-to-board connector.

The following events and controls signals (i.e., discrete signal circuit lines) are provided between the controller 36, the microcontroller 64, and other additional feature components as shown by FIG. 4. An nMEZ_PWR_EN signal is provided from the controller 36 to enable/disable power selectively to components provided on the mezzanine circuit board 22. Components to be controlled by this signal are, for example, wired connection controller 66, wireless connection controller 70, and/or charger 78 which are supplied power via a switchable power connection from the microcontroller 64. An nMAIN_INT signal is provided which is an event interrupt signal used to wake up the microcontroller 64 or request status of the microcontroller 64.

Three signals GPIO_1, GPIO_2 & GPIO_3 are provided in which each is a discrete signal and in which the combination of these discrete signals provide a status of current conditions of the microcontroller 64. In particular, these signals are utilized in conjunction with the nMAIN_INT signal to provide a means of polling the microcontroller 64 for the status of the mezzanine circuit board 22. An example of such status is provided by Table 1.

TABLE 1

| Event/Status change indications | | | |
|---|---|---|---|
| Event/State Change | GPIO_3 | GPIO_2 | GPIO_1 |
| Normal | 0 | 0 | 0 |
| Low Battery | 0 | 0 | 1 |
| Charging | 0 | 1 | 0 |
| Wired Connection | 0 | 1 | 1 |
| Wireless Connection | 1 | 0 | 0 |
| Available for future use | 1 | 0 | 1 |
| Available for future use | 1 | 1 | 0 |
| Error | 1 | 1 | 1 |

After the controller 36 asserts the nMAIN_INT signal, the microcontroller 64 responds by asserting the appropriate combination of the GPIO_1, GPIO_2 & GPIO_3 signals. After the controller 36 reads the discrete GPIO_1, GPIO_2 & GPIO_3 signals to identify the status, the controller 36 then deasserts the nMAIN_INT signal.

An nMAIN_BUSY signal is provided which is used to enable/disable communications between the controller 36 and the microcontroller 64, e.g., enable/disable the serial communications interface therebetween (i.e., board-to-board connector 24). When nMAIN_BUSY is asserted, the controller 36 is unable to respond to any events or status changes from the microcontroller 64 such as, for example, while the device 10 is conducting a blood glucose measurement or during other bGM operations that cannot be interrupted.

An nMEZ_RESET signal is provided from the controller 36, which is a control signal that resets the microcontroller 64. In addition, an nMUTE signal is provided which is used to enable/disable the serial communications interface between the controller 36 and the microcontroller 64 during operations of the controller 36 that cannot be interrupted. A SER_TXD signal is provided that is the UART output signal to the controller 36, and a SER_RXD signal is the UART input signal to the controller 36. An nMEM_RDY signal is provided which is a signal that will be HIGH when the controller 36 is ready to respond to commands from a microcontroller 64.

Two signals, CONN FAILSAFE IN & CONN FAILSAFE OUT, are used to ensure that interface between the main circuit board 20 and the mezzanine circuit board 22 via the board-to-board connector 24 is seated properly before power is applied to the controller 36 and/or microcontroller 64.

In one embodiment, the microcontroller 64 identifies to the controller 36 that an event or state has change by asserting an nMEZ_INT signal. Depending on the state of communications between the controller 36 and microcontroller 64, when the nMEZ_INT signal is asserted, the controller 36 sends a "read event" command to the microcontroller 64 when ready. The read event command is a command protocol that allows the controller 36 to determine what events and status changes the microcontroller 64 has detected. In response to receiving the read event command, the microcontroller 64 provides in one embodiment a two bits (xx) response in the output parameter, which is mapped according to Table 2, and then deasserts the nMEZ_INT signal.

TABLE 2

| Read Event Command (xx) |
|---|
| Bit Meaning |
| 0   1 = microcontroller 64 is in power on state |
|      0 = microcontroller 64 going to low power state |
| 1   1 = wired device connected to microcontroller 64 |
|      0 = wired device not connected to microcontroller 64 |
| 2   1 = microcontroller 64/wired connection controller 66 status change |
|      0 = microcontroller 64/wired connection controller 66 no status change |
| 3   1 = microcontroller 64/battery 26 status change |
|      0 = microcontroller 64/battery 26 no status change |
| 4   1 = wireless transceiver 74 muted |
|      0 = wireless transceiver 74 not muted |
| 5   1 = microcontroller 64/wireless connection controller 70 paired |
|      0 = microcontroller 64/wireless connection controller 70 not paired |
| 6   1 = microcontroller 64/wireless connection via controller 70 |
|      0 = microcontroller 64/no connection via controller 70 |
| 7   1 = microcontroller 64/wireless connection status change |
|      0 = microcontroller 64/wireless connection no status change |

In another embodiment, the controller 36 toggles the nMAIN_BUSY signal to enable/disable the communications interface as a means to acknowledge reading the event/status change signaled from the microcontroller 64. Afterwards, the microcontroller 64 then deasserts the nMEZ_INT signal and waits for the next detected status change before asserting again.

A "read battery status" command allows the controller 36 to read the status of the power supply 26. In one embodiment, the controller 36 is notified of a status change to the battery based power supply 26 with bit 3 of the read events command output shown in Table 2 with the nMEZ_INT interrupt. When ready (e.g., no other processing is on going), the controller 36 then sends the read battery status command to which the microcontroller 64 which sends a response indicating the status change. The possible responses are provided in Table 3. In one embodiment, the controller 36 toggles the nMAIN_BUSY signal to acknowledge reading the response from the microcontroller 64. Afterwards, the microcontroller 64 will deassert the nMEZ_INT signal and wait for the next detected status change before asserting the signal again.

TABLE 3

Read Battery Status Command

| Value | Status |
|---|---|
| 00 | Request to Enable Charge |
| 01 | Charging |
| 02 | Done Charging |
| 03 | Battery Low Indication |
| 04 | Battery Level Critical |
| 05 | Battery Error |
| 06-FF | Not Used |

A "read connection status" command is also provided which allows the microcontroller 64 to provide and the controller 36 to read the status of connectivity provided via either the wired connection controller 66 or the wireless connection controller 70. In one embodiment, the controller 36 is notified of a status change to the connectivity status with bit 7 of the read events command output shown in Table 2 provided with the nMEZ_INT (interrupt) signal. After receiving the nMEZ_INT signal and when ready (e.g., no other processing is on-going), the controller 36 then sends the read connection status command to which the microcontroller 64 sends a response indicating the status change. The possible responses are provided in Table 4.

TABLE 4

Read connection status

| Value | Status |
|---|---|
| 00 | Not Used |
| 01 | Not Paired |
| 02 | Pairing/Discovery Mode |
| 03 | Connecting |
| 04 | Connected |
| 05 | Connection Error |
| 06 | No Devices Available |
| 07 | Connection Timeout |
| 08 | Connection Lost |
| 09 | Disconnected |
| 0A | Transmission Acknowledged (Ack) |
| 0B | Transmission Failure |
| 0C | Request Permission for External Transmission |
| 0D-FF | Not Used |

In one embodiment, the controller 36 toggles the nMAIN_BUSY signal to acknowledge reading the response from the microcontroller 64 to the "read connection status" command. Afterwards, the microcontroller 64 will deassert the nMEZ_INT signal and wait for the next detected status change before asserting the signal again.

A control command allows the controller 36 to control/enable features or settings on the mezzanine circuit board 22 via the microcontroller 64. The control commands are defined in Table 5.

TABLE 5

Control Command

| Bit | Meaning |
|---|---|
| 0 | 1 = Enable Wireless Discovery Mode |
| | 0 = Disable Wireless Discovery Mode |
| 1 | 1 = Enable Charging of Battery |
| | 0 = Disable Charging of Battery |
| 2 | 1 = Mute Wireless transmitter |
| | 0 = Unmute Wireless transmitter |

Finally, in the above embodiment, the microcontroller 64 has a "send test results" command to request that the controller 36 send the last measurement test result for transmission. The controller 36 will either send from memory 40 the test measurement test results to the internal memory of the microcontroller 64 for transmission, or reply with a negative acknowledgement (NAK) which implies that there is no data (or incomplete data) to send. The above-described events and controls signals provided between the controllers 36, 64 during a number of use case scenarios for each of the above-mentioned modes are discussed hereafter.

In still another embodiment, memory in the communications controller 64 is used by the controller 36 to issues commands and to determine status of the communications controller 64 and/or module features on the mezzanine circuit board 22. In such an embodiment, the write and read commands have two parameters: Address—Hex Word, and Number of Bytes—Hex Word, and is implemented via a number of registers. One of such register in one embodiment is a Mezz Event Status Register 84. The Mezz Event Status Register 84 allows the controller 36 to determine what events and state changes have occurred on the mezzanine circuit board 22. In one embodiment, reading the Mezz Events Status Register 84 triggers de-assertion of the nMEZ_INT signal. The bits in the Mezz Events Status Register 84 are mapped as shown by Table 6.

TABLE 6

Mezz Events Status Register

| Bit | Meaning |
|---|---|
| 0 | 1 = Mezz CB 22 is in power on state |
| | 0 = Mezz CB 22 going to low power state |
| 1 | 1 = Mezz USB 66 connected to device |
| | 0 = Mezz USB 66 no connection |
| 2 | 1 = Mezz USB 66 status change |
| | 0 = Mezz USB 66 no status change |
| 3 | 1 = Mezz battery 26 status change |
| | 0 = Mezz no battery 26 status change |
| 4 | 1 = Mezz RF 70 muted |
| | 0 = Mezz RF 70 not muted |
| 5 | 1 = Mezz RF 70 paired |
| | 0 = Mezz RF 70 not paired |
| 6 | 1 = Mezz RF 70 connected to device |
| | 0 = Mezz RF 70 no connection |
| 7 | 1 = Mezz RF 70 connection status change |
| | 0 = Mezz RF 70 no connection status change |
| 8-15 | Not used |

In another embodiment a Battery Status Register 86 is also provided whereby a Read Mezz Battery Status command allows the controller 36 to read the current status of the battery (i.e., power supply 26). In one embodiment, the controller 36 is notified of a status change to status of the battery with bit 3 of the Read Mezz Events Command output with the nMEZ_INT interrupt, which is defined as follows by Table 7.

TABLE 7

Battery Status Register

| Value | Status |
|---|---|
| 00 | Not Used |
| 01 | Charging |
| 02 | Done Charging |
| 03 | Battery Low Indication |
| 04 | Battery Level Critical |
| 05 | Battery Error |
| 06-FF | Not Used |

In another embodiment a Mezz Connection Status Register 88 is provided. The Mezz Connection Status Registers 88 allows the controller 36 to read the current status of RF connectivity. In one embodiment, the controller 36 is notified of a status change with bit 7 of the Read Mezz Events Command output with the nMEZ_INT interrupt, which is defined as follows by Table 8.

TABLE 8

Mezz Connection Status Register

| Value | Status |
|---|---|
| 00 | RF Mute |
| 01 | Not Paired |
| 02 | Pairing/Discovery Mode |
| 03 | Connecting |
| 04 | Connected |
| 05 | Connection Error |
| 06 | No Devices Available |
| 07 | Connection Timeout |
| 08 | Connection Lost |
| 09 | Disconnected |
| 0A | Transmission Ack |
| 0B | Transmission Failure |
| 0C | Transmitting Data |
| 0D | Time/Date Synchronization Request |
| 0E-FF | Not Used |

In another embodiment a Mezz Features Register 90 is provided. The Mezz Feature Register 90 allows the controller 36 to read the features/components (rechargeable battery, RF, USB, voice, etc.) provided on the mezzanine circuit board 22. The bits of the Mezz Feature Register 90 are defined as follows in Table 9.

TABLE 9

Mezz Feature Register

| Bit | Meaning |
|---|---|
| 0 | Rechargeable Battery |
| 1 | RF Capable |
| 2 | USB Capable |
| 3 | Voice Recorder Capable |
| 4-15 | Not used |

In one embodiment, registers 84, 86, 88, and 90 are read-only.

In another embodiment, a Mezz bG Results Buffer 92 is provided. In this embodiment the Mezz Results Buffer 92 is used by controller 36 to write the last bG result automatically after each test such that it is immediately available to the communications controller 64. The bytes of the results buffer 92 is shown by Table 10.

TABLE 10

Results Buffer

| Byte(s) | Meaning | Range |
|---|---|---|
| 1-2 | Strip Count | 0-65535 |
| 3-4 | bG Result | 0-999 |
| 5-6 | Date | 010101-311231 |
| 7 | Time | 0-2359 |
| 8-9 | Flags | See Serial Comm Doc. |

In still another embodiment, a Mezz Control Register 94 is provided which allows the controller 36 to control/enable/read features or settings on the mezzanine circuit board 22. The Mezz Control Register 94 is Read and Write capable, and the bits are defined as follows in Table 11.

TABLE 11

Mezz Control Register

| Bit | Meaning |
|---|---|
| 0 | 1 = Enable RF Discovery Mode<br>0 = Disable RF Discovery Mode |
| 1 | 1 = Enable Time & Date Synchronization<br>0 = Disable Time & Date Synchronization |
| 2 | 1 = Mute RF transmitter<br>0 = Unmute RF transmitter |
| 3-15 | Not used |

It is to be appreciated that in other embodiments, the mezzanine circuit board 22 may provide a separate memory for the registers 84, 86, 88, 90 and 94 and buffer 92. In one embodiment, the feature register 92 is read by the controller 36 upon power up to set the firmware interaction behavior between the main circuit board 20 and the features present on the mezzanine circuit board 22. Such an embodiment may be used for external translation purposes without the need for changing the main meter base communication protocols. The translation layer would be resident on the mezzanine circuit board 22 and be feature dependant thus allowing the mezzanine architecture to quickly adapt to new emerging connectivity options. Accordingly, such embodiments described above allow the ability to add a new capability (such as wireless, voice recording, etc.) without the main circuit board 20 carrying the extra cost, wherein the cost is resident on the mezzanine circuit board 22.

In the following use cases, it is assumed that the device 10 has gone through a successful power-on. In a power down use case, the following firmware interactions take place after either a user initiates a power down of the device 10 (e.g., toggling of the on/off button) or expiration of a programmed inactivity timer of the device 10.

If the device 10 is programmed according to the LOW F/W interaction configuration mode, in a power down use case the controller 36 will assert the nMAIN_INT signal to wake up the microcontroller 64. Next, the controller 36 will deassert the nMEM_RDY signal to indicate that it is no longer ready to respond to commands from the microcontroller 64. Upon the nMEM_RDY signal going low, the microcontroller 64 power downs the components of the mezzanine circuit board 22 and goes into a low power mode.

If the device 10 is programmed according to the MEDIUM F/W interaction configuration mode, in the power down use case the controller 36 will assert the nMAIN_BUSY signal to disable any currently on-going communications between the controller 36 and the microcontroller 64. Next, the controller 36 deasserts the nMEM_RDY signal to indicate that it is no longer ready to respond to commands from the microcontroller 64. Upon the nMEM_RDY signal going low, the microcontroller 64 power downs the components of the mezzanine circuit board 22 and goes into a low power mode.

If the device 10 is programmed according to the HIGH F/W interaction configuration mode, in the power down use case initiated via the user, the controller 36 will deassert the nMEZ_PWR_EN signal to selectively power down components of the mezzanine circuit board 22. Next, the controller 36 asserts the nMUTE signal to disable the serial communications interface between the controller 36 and the microcontroller 64 as well as deasserting the nMEM_RDY signal. Upon the nMEM_RDY signal going low, the microcontroller 64 power downs to a low power mode.

In the situation when the power down is do to inactivity, after expiration of the inactivity timer, the microcontroller 64 will assert the nMEZ_INT signal to identify to the controller 36 that an event or state has changed. The controller 36 will send a read event command to the microcontroller 64, which responds with the appropriate event code (e.g., Table 2, "00" microcontroller 64 going to low power state) and deassert the nMEZ_INT signal. The controller 36 will then deassert the nMEZ_PWR_EN signal and assert the nMUTE signal, and go into a low power mode.

In all the above configuration modes, after powering down, both the controller 36 and the microcontroller 64 are in a low power mode. In such a state, both the controller 36 and the microcontroller 64 can be waken via an interrupt event, service the request, and restore back to the low-power mode on return from the interrupt program. Such a low power arrangement is useful in a wired wake-up use case described hereafter.

In one embodiment, when a user connects via the wired connection 68 the external device 27 to the device 10, the wired connection controller 66 will send an interrupt event to the microcontroller 64 and perform a wired connection setup according to standards. The microcontroller 64 after receiving the interrupt event will then asserts the nMEZ_INT signal to wake up the controller 36 by identifying to the controller 36 that an event or state has changed. The controller 36 then asserts the nMAIN_INT signal to request the attention of the microcontroller 64. Afterwards, the microcontroller 64 asserts the nMEM_RDY signal to indicate that it is ready to respond to commands from the microcontroller 64.

After the above initial interactions, if the device 10 is programmed according to the LOW F/W interaction configuration mode, the controller 36 will establish a serial communication session with the microcontroller 64. For the serial communication session, if the microcontroller 64 is connected properly via the board-to-board connector 24, the microcontroller will send the CONN FAILSAFE IN signal to the controller 36 which responds with an acknowledgement signal (e.g., ACK or NAK). After which, the controller 36 and microcontroller 64 will send each other read, clear, and status messages and provide user notifications of any events and/or status of the serial communication session.

In another embodiment, all the above interactions also occur in the LOW F/W interaction configuration mode whenever an external device is wire connected to device 10 even if the device 10 is already powered on. In still a further embodiment, a speech emulation/recognition module 63 is provided to the mezzanine circuit board 22 as an additional feature. In this embodiment, the emulation/recognition module 63 is enabled, for example, via user selection from a features menu presented on the display 12. If, in this embodiment when the emulation/recognition module 63 is enabled, then the microcontroller 64 will monitor for serial communications activity (e.g., voice commands) unless the user is performing a measurement test (e.g., blood glucose test via strip reading) and a sufficient sample has been detected by the strip reader 48 in this mode.

If the device 10 is programmed according to the MEDIUM F/W interaction configuration mode, then generally the device 10 will wake up and automatically ready the controller 36 and microcontroller 64 for communications with the wired external device 27. After the above-mentioned initial interactions, the controller 36 will send a read event command to the microcontroller 64, which responds with the appropriate event code to indicate what type of a USB connection (e.g., Table 2, "11"). Next, the controller 36 will toggle the nMAIN_BUSY signal to enable/disable communications between the controller 36 and the microcontroller 64 and deasserts the nMEZ_INT signal. The controller 36 will then establish the serial communication session with the microcontroller 64. In another embodiment, the above interactions will also take place in this mode whenever an external device is wired connected to device 10 even if the device 10 is already powered on.

If the device 10 is programmed according to the HIGH F/W interaction configuration mode, then after the above-mentioned initial interactions, the controller 36 will also deassert the nMUTE signal to enable the serial communications interface between the controller 36 and the microcontroller 64.

In one embodiment, the device 10 may also be powered on by a user. When the device 10 is powered on by the user (e.g., use of an on/off switch or button combination, for example, holding LEFT and RIGHT button for a designated time, e.g., 3 seconds), the controller 36 wakes up and asserts the nMEM_RDY signal which wakes up the microcontroller 64. In this power on use case, the controller 36 also deasserts the nMAIN_BUSY signal to enable the serial communication session between the controller 36 and the microcontroller 64. Next, the microcontroller 64 will assert the nMEZ_INT signal to indicate a status change. The controller 36 will then send a read event command to the microcontroller 64, which responds with the appropriate event code to indicate that all is normal (e.g., Table 2, "01"-powered on). Next, the controller 36 will toggle the nMAIN_BUSY signal to acknowledge reading the response to the read event command, wherein the microcontroller 64 deassert the nMEZ_INT signal such that the device 10 is ready for use.

In the embodiments discussed hereafter it is assumed that the device 10 has successfully powered on (wake up or user initiated) and started up the serial communication session. Thereafter, the microcontroller 64 in both the LOW and MEDIUM F/W configuration mode, and if so enabled in the HIGH F/W Interaction configuration mode, will enter into a communication controller mode to establish a communications connection with an external device (wired or wireless). It is to be appreciated that the microcontroller 64 will provide the controller 36 status of the connection. For example, when a connection is established, the microcontroller 64 will send to the controller 36 the "read connection status" command indicating that a connection is made ("04", Table 4). The controller 36 then responds with an acknowledgement (ACK) signal. After which, the controller 36 and microcontroller 64 send each other read, clear, and status command messages and, when necessary, provide user notifications of any events and/or status of the communication session with the external device. The external device 27, the microcontroller 64, and the controller 36 then carry out buffered communications automatically in one embodiment.

In one embodiment, the user notification is performed by the microcontroller sending the controller 36 a write command to display the status on the display 12. The controller 36 acknowledges (e.g., responds with the acknowledgement signal), and then utilizes a display driver to display the event/status on the display 12. In other embodiments, the user responses and/or provides instructions to the microcontroller 64 via the user interface in response to the status/event display, if desired.

In one embodiment, in response to the microcontroller 64 indicating a change in battery status e.g., bits "31", Table 2, provided with the microcontroller interrupt (nMEZ_INT) signal, the controller 36 will send the read battery status command. In response, the microcontroller 64 sends a request battery charging response ("00", Table 3), for example, in one embodiment if the battery gage indicates that the remaining charge on the power supply 26 is below a predetermined level (e.g., less than 50%). After the controller 36 toggles the nMAIN_BUSY signal to acknowledge reading the response from the microcontroller 64, and the microcontroller 64 has deasserted the nMEZ_INT signal, the controller 36 then sends the command control that battery charging is allowed or not ("11" or "10", respectively, Table 5). If allowed, the microcontroller 64 will acknowledge and start charging of the power supply via enabling the charger 78, or via the USB connection.

If attempting to charge via the wired connection 68, and if the external device 27 is capable of charging, e.g., via the universal connection such as USB or Firewire, the microcontroller 64 after being allowed to charge again asserts the nMEZ_INT signal to indicate a status change. The controller 36 will then send a read event command to the microcontroller 64, which responds with the appropriate event code to indicate a change in battery status (e.g., Table 2, "31"). Next, the controller 36 will toggle the nMAIN_BUSY signal to acknowledge reading the response to the read event command, wherein the microcontroller 64 deassert the nMEZ_INT signal. Next, the controller 36 sends the "read battery status" command, to which the microcontroller 64 responds in this use case with a charging message (e.g., Table 3, "01") and the controller 36 acknowledges. If, however, the external device 27 is not capable of charging, then microcontroller may respond with a low battery message, or even a critically low battery message. In one embodiment, the controller 36 displays the received battery status message on the display 12 in order to notify the user of the battery state. This display of battery state may also be done whenever the controller 36 receives a change in battery status from the microcontroller 64. After that point, the microcontroller 64 will inform the controller 36 of any status change e.g., done charging, error, or wired/wireless connection disconnect, via the nMEZ_INT signal as previously explained above for other such status changes.

In another embodiment, after the device 10 has successfully powered on (wake up or user initiated) and started up the serial communication session, if a first time user is using the device 10 with the external device 27 via a wireless connection 72, then the device 10 will enter into a first time user set-up mode. In the set-up mode, the user will be presented on the display 12 with set-up options (e.g., enter a personal identification number, type of wireless device, etc.) to enable the wireless communication with the external device 27. The user selects the set-up options using the user interface 32 e.g., via the buttons and/or touch search interface, and then enables the wireless capability of the device 10, which launches an autonomous pairing, connection, and transmission process.

Figure 5:
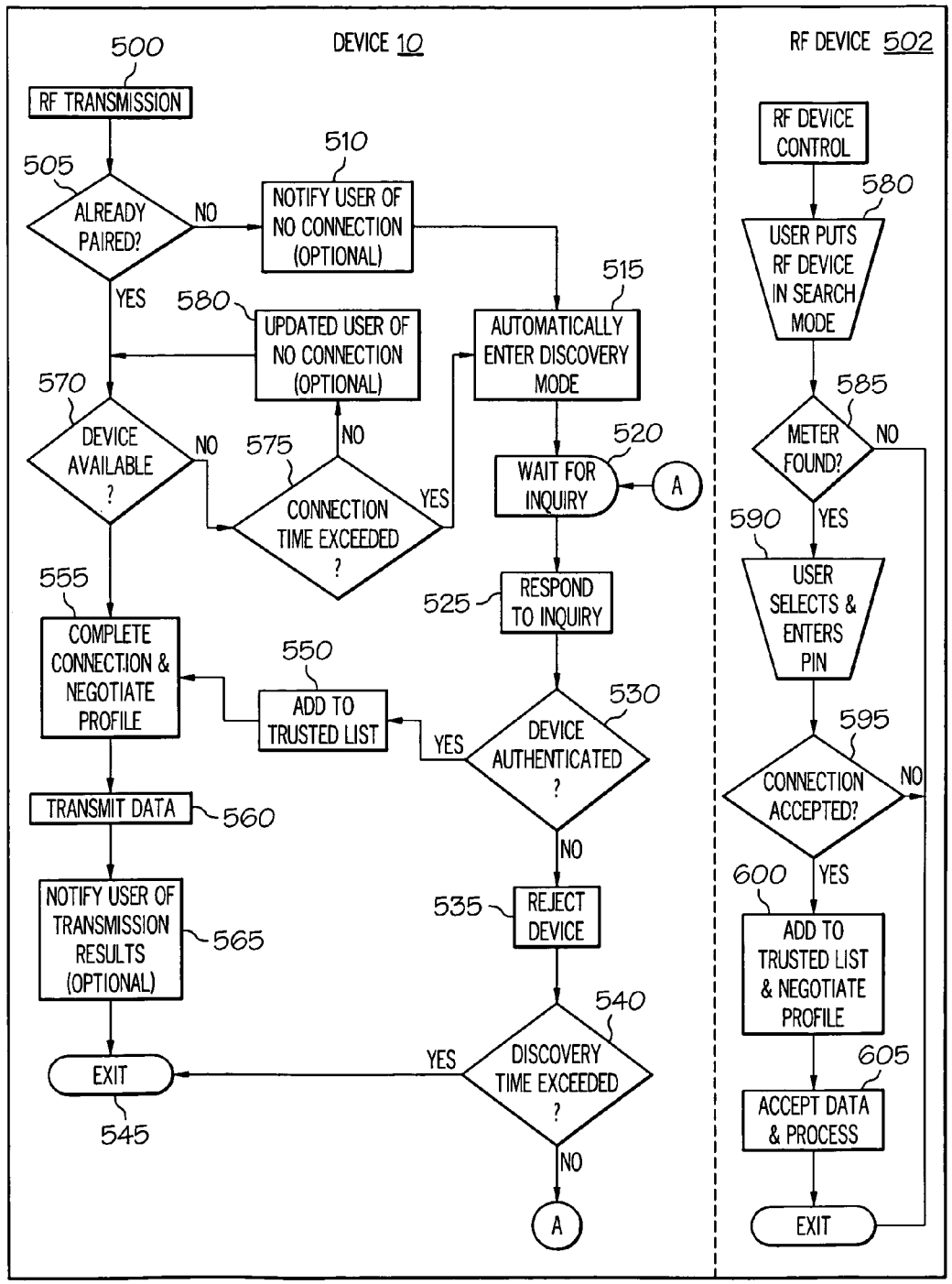
FIG. 5 is a flow chart showing a process embodiment according to the present invention showing an autonomous device pairing, connection, and transmission.

The autonomous pairing, connection & transmission process 500 is depicted by the flow chart of FIG. 5. As shown, in step 505, when a wireless transmission is to take place by the device 10, the microcontroller 64 checks to see if a communication connection with an external wireless device 502 (via wireless connection controller 70, FIG. 3) is paired (connected) thereto. If the status check is no, then in optional step 510 the user is notified via the display 12 (as controlled by the controller 36) that no wireless connection is detected. Next, in step 515 the microcontroller 64 automatically places the wireless connection controller 70 in the discovery mode, wherein the wireless connection controller 70 responds to connection inquires with a device name in order to identify the device 10 to the external wireless device 502.

In one embodiment, the discovery mode is enabled by the controller 36 sending the microcontroller 64 a control command to enter the discovery mode (e.g., "01", Table 5), which the microcontroller 64 acknowledges and turns on the wireless controller 70 as indicated above. Accordingly, afterwards if no error, the microcontroller 64 should again assert the nMEZ_INT signal to indicate a status change. The controller 36 will then send a read event command to the microcontroller 64, which responds with the appropriate event code to indicate that the wireless connection controller 70 is paired (connected) with the microcontroller 64 and that the status of the connection device has changed (e.g., Table 2, "51" and "71", respectively). Next, the controller 36 will toggle the nMAIN_BUSY signal to acknowledge reading the response to the read event command, wherein the microcontroller 64 deassert the nMEZ_INT signal. Next, the controller 36 sends the read connection status command, to which the microcontroller 64 responds with the appropriate connection status message (e.g., in the discover mode, "01", Table 4) and the controller 36 acknowledges. In one embodiment, the user is notified on the latest connection status message on the display 12.

Referring back to FIG. 5, the microcontroller in step 520 then waits for a connection inquiry from the external wireless device. For example, in one embodiment, the user may be informed on the display 12 that the device 10 is in a discovery mode waiting a connection inquiry from the external wireless device 502. At this point, the user may be required to power on and place the external wireless device in a search mode in order to send at a connection inquiry to the device 10.

When in step 525 an inquiry is made from the external wireless device 502, the microcontroller 64 then checks in step 530 whether the inquiring wireless device has authorization via receiving an entered personal identification number (PIN) or some other identification means from the external wireless device 502. For example, after the wireless device finds the device 10, the user may need to select the meter for connection and enter the PIN previously enter in the device 10 during set-up. In step 535, if the PIN is not acceptable, then the microcontroller 64 will reject the connection inquiry and then checks to see if a discovery time is exceeded in step 540. If the discovery time is not exceeded, then the microcontroller 64 returns to step 520 and waits for another connection inquiry in which to authenticate. If, however, the discovery time is exceeded, then the discovery mode is exited in step 545.

If the authentication in step 530 is valid, then the microcontroller 64 adds the external wireless device 502 to a trusted list stored in memory in step 550. In one embodiment, the controller 36 may prompt the user on the display 12 to accept the connection. If the user response affirmatively via the user interface 32, then step 550 is completed, otherwise the discovery mode is exited in step 545. Next in step 555, the microcontroller 64 via the wireless connection controller 70 completes a connection negotiation (e.g., according to a profile) to ready the wireless device for receipt of data and transmits the data in step 560.

For example, in one embodiment, when the connection negotiation is completed, the microcontroller 64 will assert the nMEZ_INT signal to indicate a status change. The controller 36 will then send a read event command to the microcontroller 64, which responds with the appropriate event code to indicate that the wireless connection controller 70 is paired (connected) with the microcontroller 64 and that the status of the connection device has changed (e.g., Table 2, "51" and "71", respectively). Next, the controller 36 will toggle the nMAIN_BUSY signal to acknowledge reading the response to the read event command, wherein the microcontroller 64 deassert the nMEZ_INT signal. Next, the controller 36 sends the "read connection status" command, to which the microcontroller 64 responds with the appropriate connection status message (e.g., "02"-connecting, "03"-connected, etc., Table 4) and the controller 36 acknowledges. In one embodiment, the user is notified on the latest connection status message on the display 12.

Returning to FIG. 5, after connecting with the external wireless device 502, the external device and device 10 carry out buffered communications via the wireless connection. In one embodiment, after negotiating the connection, data containing the results of the blood glucose measurement are transferred from memory of the device 10 to memory of the external wireless device. The microcontroller 64 then in step 565 notifies the user on the display 12 (via the controller 36) of any updated status and/or results of the transmission (e.g., successful, failed, etc.) via the microcontroller 64 using the nMEZ_INT signal to indicate all status changes to the controller 36 in a similar manner as explained above in the previous section.

It is to be appreciated that the connection and transmission steps 555 and 560, respectively, likewise may be completed if the pairing between the microcontroller 64 (via the wireless connection controller 70) and the external wireless device is affirmed in step 505. If affirmed in step 505, then in step 570, the microcontroller 64 checks to see if the wireless device is available in which to complete steps 555-565. If not, then in step 575, the microcontroller 64 checks to see if the connection time has been exceeded. If yes, then the microcontroller 64 performs the automatic discovery mode detailed by steps 515-540. If no, then in optional step 580 the user is notified of the unavailability of the wireless device via the display 12 (under the control of the controller 36), and rechecks whether the external wireless device 502 is available in step 570 thereafter.

The above autonomous pairing, connection & transmission process 500 assumes that the user has placed or configured the wireless device in a search mode in step 580. In the search mode, the external wireless device 502 sends out the inquiry signal and in step 585 checks if the device 10 responds to the inquiry. If no response is received, the wireless device 502 exits the search mode. If a response is received, then in step 590 the user transmits the PIN and sees if it is accepted by the device 10 in step 595. If not, the wireless device 502 exits the search mode or if accepted, then the wireless device adds the device 10 to a trusted list and completes the connection negotiation profile to ready the device 10 for the transmission of data in step 600. Data is then received by the wireless device in step 605.

In one embodiment, after notifying the user of the data transmission, the controller 36 then in one embodiment may deassert the nMEZ_PWR_EN signal to turn off the components of the mezzanine circuit board and place the microcontroller 64 in the low power mode by deasserting the nMEM_RDY signal. Accordingly, in this embodiment, the connection to the external wireless device 502 is terminated.

In another embodiment, if after expiration of a period wherein no data has been transmitted or received over the wired or wireless connection 68 or 73, respectively, the microcontroller 64 asserts the nMEZ_INT signal to indicate a status change. The controller 36 will then send a read event command to the microcontroller 64, which responds with the appropriate event code to indicate that it is going to the low power state (e.g., Table 2, "00"). Next, the controller 36 will toggle the nMAIN_BUSY signal to acknowledge reading the response to the read event command, wherein the microcontroller 64 deassert the nMEZ_INT signal and goes into the low power state. In another embodiment, the controller 36 deasserts the nMEM_RDY signal such that the controller 36 is no longer ready to respond to commands from a microcontroller 64.

Another use case of the device 10 is performing a measurement test, such as a blood glucose test in one embodiment and any other type of physiological measurement test suitable for performing on a portable medical device in other embodiments. In one embodiment, the device 10 is configured to transmit automatically to an external device the result of a measurement test, such as for example, a blood glucose level and other associated data of the test. After the user has initiated the measurement test, in one embodiment the controller 36 asserts the nMAIN_BUSY signal such that the microcontroller 64 is notified that the controller 36 is busy. In another embodiment, the controller 36 asserts the nMUTE signal to disable the serial communications interface between the controller 36 and the microcontroller 64, and then deasserts the nMEZ_PWR_EN signal, which will end any communications ongoing with an external device by powering down the wired and/or wireless connection controller 66 and 70, respectively. The latter embodiment is performed when the device 10 is performing an operation that cannot be interrupted, such as the blood glucose test.

In another embodiment, if the nMUTE signal is not asserted by the controller 36, then after the nMEZ_PWR_EN signal is deasserted, the microcontroller 64 will assert the nMEZ_INT signal to indicate a change in status to the controller 36. The controller 36 will then send a "read event" command to the microcontroller 64 to which the microcontroller responds with the appropriate event code to indicate that the status has changed. For example, the event code may be either "21"-microcontroller 64/wired controller 66 status change, "41"-wireless transceiver 74 muted, or "50"-microcontroller 64/wireless controller 70 not paired in Table 2, which depends on the flavor of the components provided on the mezzanine circuit board 22. Next, the controller 36 will toggle the nMAIN_BUSY signal to acknowledge reading the response to the read event command, wherein the microcontroller 64 deassert the nMEZ_INT signal. This embodiment is performed whenever the user instructs the device 10 to mute communications, such for example, via the user interface 32.

After the controller 36 has completed the measurement test, in one embodiment the controller 36 then deasserts the nMAIN_BUSY signal, and sends the last results of the measurement test to the microcontroller 64 for transmission to the external device. If a connection with the external device is not enabled, then in one embodiment the device 10 performs the autonomous, pairing, connection and transmission process 500 (FIG. 5) in order to complete the transmission.

In another embodiment, after the controller 36 has completed the measurement test, the controller deasserts the nMUTE signal, which causes the serial communication session between the controller 36 and microcontroller 64 to be restored. The controller 36 then asserts the nMEZ_PWR_EN signal to enable power selectively to components provided on the mezzanine circuit board 22. The microcontroller 64 afterwards asserts the nMEZ_INT signal to indicate a change in status to the controller 36. The controller 36 will then send a "read event" command to the microcontroller 64 to which the microcontroller 64 responds with the appropriate event code to indicate that the status has changed. In this case, for example, the event code may be either "21"-microcontroller 64 and wired connection controller 66 status change (implying pairing), or "51"-microcontroller 64 and wireless connection controller 70 pairing, depending on the flavor of components provided on the mezzanine circuit board 22. Next, the controller 36 will toggle the nMAIN_BUSY signal to acknowledge reading the response to the read event command, wherein the microcontroller 64 deassert the nMEZ_INT signal. This embodiment would typically be done when the controller 36 has completed an operation that had previously caused the serial communications between the microcontroller 64 and the controller 36 to be muted.

Continuing with the above embodiment, after the serial communication session has been restored, the controller 36 then asserts the nMAIN_INT signal to get connection status of the microcontroller 64, which implies that a new event has occurred, i.e., completion of the measurement test. After the controller 36 asserts the nMAIN_INT signal, the microcontroller 64 responds by asserting the appropriate combination of the GPIO_1, GPIO_2 & GPIO_3 signals to indicate which type of connection is available (either "011"-wired or "100"-wireless, Table 1). After the controller 36 reads the discrete GPIO_1, GPIO_2 & GPIO_3 signals to identify the connection status, the controller 36 then deasserts the nMAIN_INT signal. Next, the microcontroller 64 sends the microcontroller 64 the send test results command to request that the controller 36 send the last measurement test result for transmission. As mentioned previously, the controller 36 will either send the test measurement results to the microcontroller 64 for transmission, or reply with a negative acknowledgement (NAK) to indicate that there is no data (or incomplete data) to send. If receiving data, the microcontroller 64 then transmits the data to the external device, via completing the autonomous, pairing, connection and transmission process 500 (FIG. 5).

The above description and drawings are only to be considered illustrative of exemplary embodiments, which achieve the features and advantages of the present invention. Modification and substitutions to specific process steps, system, and setup can be made without departing from the spirit and scope of the present invention. Accordingly, the invention is not to be considered as being limited by the foregoing description and drawings, but is only limited by the scope of the appended claims.

What is claimed is:

1. A portable handheld medical diagnostic device capable of communicating with an external device, said diagnostic device comprising:

a protective enclosure;
a power supply disposed within the protective enclosure:
a main circuit board provided in the protective enclosure and having a wireless connectivity component and a controller, wherein the wireless connectivity component establishes a communication link between the main circuit board and the external device, the controller facilitates a physiologic measurement and communications of results of the physiological measurement to the external device, and the controller is configured to disable the wireless connectivity component automatically during the physiological measurement;
a mezzanine circuit board provided in the protective enclosure and having at least one of a plurality of additional feature modules and a communications microcontroller, wherein the communications microcontroller is programmed to operate the at least one additional feature module and to operate under the control of the controller of the main circuit board, the controller controls operation of the at least one of additional feature modules via the communications microcontroller such that the communications microcontroller performs as a control interface between the controller and the at least one additional feature module;
a board-to-board connector electrically connecting the mezzanine circuit board to the main circuit board, the board-to-board connector comprising a power circuit line and one or more fail-safe circuit lines; and
a regulator disposed on the mezzanine circuit board and electrically connected to the power circuit line of the board-to-board connector and the power supply.

2. The portable handheld medical diagnostic device according to claim 1 wherein the at least one additional feature module establishes communications and optionally an electrical connection with the external device such that the controller is enabled to transmit results of the physiological measurement to the external device by sending the results to the at least one additional feature module via the communications microcontroller.

3. The portable handheld medical diagnostic device according to claim 1 wherein the at least one additional feature module establishes communications and an electrical connection with the external device such that the controller is enabled to recharge the power supply and transmit results of the physiological measurement to the external device by sending the results to the at least one additional feature module via the communications microcontroller.

4. The portable handheld medical diagnostic device according to claim 1 wherein the board-to-board connector electrically connects the mezzanine circuit board to the main circuit board in a stacked fashion that situates major surfaces of both the main board and the mezzanine circuit board in close proximity within the protective enclosure.

5. The portable handheld medical diagnostic device according to claim 1 wherein the at least one additional feature module comprises a wired connection controller, a wireless connection controller, a speech emulation/recognition module, a voice recorder module, a RF telemetry module, a GPS module, a memory device, a camera module, a battery-charging/power module, and combinations thereof.

6. The portable handheld medical diagnostic device according to claim 1 wherein the wireless connectivity component is an IrDA device, and the at least one additional feature module is a wireless connection controller.

7. The portable handheld medical diagnostic device according to claim 1 wherein the wireless connectivity component is an IrDA device, and the at least one additional feature module is a wireless connection controller, and wherein the wireless connection controller is selected from the group consisting of a Bluetooth system, a ZigBee system, a Certified Wireless USB system device, a Near Field Communication (NFC) system, an Active RFID system, a FitLinxx system, and a Wi-Fi system.

8. The portable handheld medical diagnostic device according to claim 1 wherein the wireless connectivity component is selected from the group consisting of a Bluetooth system, a ZigBee system, a Certified Wireless USB system, a Near Field Communication (NFC) system, an Active RFID system, a FitLinxx system, a Wi-Fi system, and an IrDA device.

9. The portable handheld medical diagnostic device according to claim 1 wherein the wireless connectivity component is selected from the group consisting of a Bluetooth system, a ZigBee system, a Certified Wireless USB system, a Near Field Communication (NFC) system, an Active RFID system, a Wi-Fi system, a FitLinxx system, and an IrDA device and wherein the at least one additional feature module comprises a wired connection controller, a wireless connection controller different from the wireless connectivity module, a speech emulation/recognition module, a voice recorder module, a RF telemetry module, GPS module, a memory device, a camera module, a battery-charging/power module, and combinations thereof.

10. The portable handheld medical diagnostic device according to claim 1 wherein the wireless connectivity component is selected from the group consisting of a Bluetooth system, a ZigBee system, a Certified Wireless USB system, a Near Field Communication (NFC) system, an Active RFID system, a Wi-Fi system, a FitLinxx system, and a IrDA device, and the at least one additional feature module is a wireless connection controller selected from the group consisting of a Bluetooth system, a ZigBee system, a Certified Wireless USB system, a Near Field Communication (NFC) system, a FitLinxx system, an Active RFID system, a Wi-Fi system, and a IrDA device.

11. The portable handheld medical diagnostic device according to claim 4 wherein the board-to-board connector provides a space between the major surface plans of the boards that is less than 0.8-inch.

12. The portable handheld medical diagnostic device according to claim 1 wherein the physiologic measurement is a blood glucose measurement.

13. The portable handheld medical diagnostic device according to claim 1 wherein the physiologic measurement is a recording of food intake, exercise, sleep patterns, drug(s) intake, therapy completion, and combinations thereof.

14. The portable handheld medical diagnostic device according to claim 1 wherein the physiologic measurement is a recording of blood oxygen, body temperature, heart rate, caloric expenditure, and combinations thereof.

15. The portable handheld medical diagnostic device according to claim 1 wherein the at least one additional feature module is a wired connection controller that enables a wired connection to the external device.

16. The portable handheld medical diagnostic device according to claim 15 wherein the wired connection controller is based on a standard selected from universal serial bus (USB) and a Firewire.

17. The portable handheld medical diagnostic device according to claim 1 wherein the at least one additional feature module is a wireless connection controller that enables a wireless connection to the external device.

18. The portable handheld medical diagnostic device according to claim 1 wherein the external device comprises a computer, a PDA, a scanner, a digital camera, a webcam, a printer, a communications hub/adapter, additional memory, a smart card reader, a flash drive, a human-interface device, a sensor, a second power supply, and combinations thereof.

19. The portable handheld medical diagnostic device according to claim 1 wherein the protective enclosure comprises a rear housing, and the main circuit board and the mezzanine circuit board are situated in a cavity provided by the rear housing.

20. The portable handheld medical diagnostic device according to claim 1 wherein the major surfaces of the main circuit board and the mezzanine circuit board are in parallel planes.

21. The portable handheld medical diagnostic device according to claim 1 wherein the communications microcontroller operates under the control of the controller via a set of commands and event/status signals.

22. The portable handheld medical diagnostic device according to claim 1 wherein the communications microcontroller operates under the control of the controller via a set of commands and event/status signals comprising a signal that permits the controller to power selectively the at least one additional feature module.

23. The portable handheld medical diagnostic device according to claim 1 wherein the communications microcontroller operates under the control of the controller via a set of commands and event/status signals comprising a signal that permits the controller to wake up the microcontroller and request status of the microcontroller.

24. The portable handheld medical diagnostic device according to claim 1 wherein the communications microcontroller operates under the control of the controller via a set of commands and event/status signals comprising three signals that the microcontroller uses in various high and low combinations to indicate current conditions of the microcontroller to the controller.

25. The portable handheld medical diagnostic device according to claim 1 wherein the communications microcontroller operates under the control of the controller via a set of commands and event/status signals comprising a signal that permits the controller to enable or disable communications between the controller and the microcontroller.

26. The portable handheld medical diagnostic device according to claim 1 wherein the communications microcontroller operates under the control of the controller via a set of commands and event/status signals comprising a signal that permits the controller to reset the microcontroller.

27. The portable handheld medical diagnostic device according to claim 1 wherein the communications microcontroller operates under the control of the controller via a set of commands and event/status signals comprising a signal that permits the controller to enable or disable a serial communications interface between the controller and the microcontroller during the physiologic measurement.

28. The portable handheld medical diagnostic device according to claim 1 wherein the communications microcontroller operates under the control of the controller via a set of commands and event/status signals comprising input and output signals that permits the controller to communicate with the external device via routing the input and output signals through the communications microcontroller.

29. The portable handheld medical diagnostic device according to claim 1 wherein the communications microcontroller operates under the control of the controller via a set of commands and event/status signals comprising a signal that when asserted by the controller lets the microcontroller know that the controller is ready to respond to requests from a microcontroller.

30. The portable handheld medical diagnostic device according to claim 1 wherein the communications microcontroller operates under the control of the controller via a set of commands and event/status signals comprising signals that permits the controller to ensure that the board-to-board connector between the main circuit board and the mezzanine circuit board is seated properly.

31. The portable handheld medical diagnostic device according to claim 1 wherein the communications microcontroller operates under the control of the controller via a set of commands and event/status signals comprising a signal that permits the microcontroller to identify to the controller that an event or state has changed.

32. The portable handheld medical diagnostic device according to claim 31 wherein the set of commands and event/status signals further comprises a command that permits the controller to determine what events or status change the microcontroller has detected.

33. The portable handheld medical diagnostic device according to claim 1 wherein a register is used by the controller to determine status of the microcontroller and the additional feature module.

34. The portable handheld medical diagnostic device according to claim 1 wherein a result buffer on the mezzanine circuit board is used by the controller to store and provide the results of the physiological measurement.

35. The portable handheld medical diagnostic device according to claim 1 wherein a register is used by the controller to control the microcontroller and the additional feature module.

36. The portable handheld medical diagnostic device according to claim 1 wherein the communications microcontroller operates under the control of the controller via a set of commands and event/status signals comprising a command that permits the controller to read the current status of the power supply.

37. The portable handheld medical diagnostic device according to claim 1 wherein the communications microcontroller operates under the control of the controller via a set of commands and event/status signals comprising a command that permits the microcontroller to provide and the controller to read current status of connectivity with the external device via the additional features module.

38. The portable handheld medical diagnostic device according to claim 1 wherein the communications microcontroller operates under the control of the controller via a set of commands and event/status signals comprising a command which permits the controller to control features or settings on the mezzanine circuit board via the microcontroller.

39. The portable handheld medical diagnostic device according to claim 1 wherein the communications microcontroller operates under the control of the controller via a set of commands and event/status signals comprising a command that permits the microcontroller to request that the controller send results of the physiologic measurement for transmission to the external device via the additional feature module.

40. A portable handheld medical diagnostic device capable of communicating with an external device, said diagnostic device comprising:
   a protective enclosure;
   a power supply disposed within the protective enclosure:
   a main circuit board provided in the protective enclosure and having a wireless connectivity component and a controller, wherein the wireless connectivity establishes a communication link between the main circuit board and the external device, the controller facilitates a physiologic measurement and communicates results of the physiological measurement to the external device, and the controller is configured to disable the wireless connectivity component automatically during the physiological measurement;
   a mezzanine circuit board provided in the protective enclosure and having at least one additional feature module and communication means, wherein the communication means is programmed to facilitate operation of the at least one additional feature module and to operate under the control of the controller of the main circuit board via a set of commands and event/status signals, wherein the set of commands and event/status signals transmitted by the controller comprises a signal that permits the controller to power selectively the at least one additional feature module;
   a board-to-board connector electrically connecting the mezzanine circuit board to the main circuit board, the board-to-board connector comprising a power circuit line and one or more fail-safe circuit lines; and
   a regulator disposed on the mezzanine circuit board and electrically connected to the power circuit line of the board-to-board connector and the power supply, wherein when the one or more fail-safe circuit lines detect that the board-to-board connector is properly seated, system power is transmitted automatically to the controller of the main circuit board from the regulator of the mezzanine circuit board via the power circuit line of the board-to-board connector.

* * * * *